United States Patent [19]

Mohan et al.

[11] Patent Number: 5,342,944
[45] Date of Patent: Aug. 30, 1994

[54] PROCESS FOR THE PREPARATION OF 2-ALKYL-3,5,6,7- OR 8-SUBSTITUTED-4(3H)-QUINAZOLINONES

[75] Inventors: Arthur G. Mohan, Somerville; Joseph D'Antuono, III, Three Bridges, both of N.J.

[73] Assignee: American Cyanamid Company, Wayne, N.J.

[21] Appl. No.: 92,850

[22] Filed: Jul. 19, 1993

[51] Int. Cl.[5] .................. C07D 239/90; C07D 239/91
[52] U.S. Cl. ..................................... 544/284; 544/287
[58] Field of Search .......................... 544/284, 287

[56] References Cited

U.S. PATENT DOCUMENTS 5,238,942  8/1993  Chakravarty et al. .............. 514/259
5,240,928  8/1993  Allen et al. ......................... 514/259

FOREIGN PATENT DOCUMENTS 253310  1/1988  European Pat. Off. .
324377  7/1989  European Pat. Off. .
497150  8/1992  European Pat. Off. .

*Primary Examiner*—Mukund J. Shah
*Assistant Examiner*—Matthew V. Grumbling
*Attorney, Agent, or Firm*—Kenneth J. Dow

[57] ABSTRACT

A novel process for producing 2-alkyl-3,5,6,7 or 8-substituted-4 (3H)-quinazolinones of the formula:

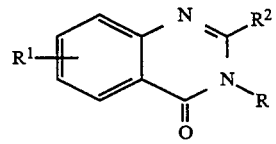

where R, $R^1$ and $R^2$ are defined in the specification by reacting the appropriately N-acyl substituted aminobenzoic acids with ethylchloroformate followed by further reaction with ammonia or a primary amine.

6 Claims, No Drawings

PROCESS FOR THE PREPARATION OF 2-ALKYL-3,5,6,7- OR 8-SUBSTITUTED-4(3H)-QUINAZOLINONES

BACKGROUND OF THE INVENTION

1. Field of the Invention

The invention relates to a novel process for the preparation of 2-alkyl-3,5,6,7 or 8 -substituted-4(3H)-quinazolinones. This process has the advantages of providing a high yield of a purer product in a more efficient and less costly way.

2. Description of the Prior Art

The compounds prepared by the process of the present invention, namely the 2-alkyl-3,5,6,7 or 8 -substituted-4(3H)-quinazolinone compounds of the following formula:

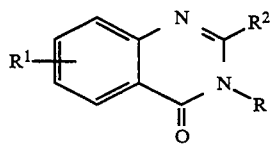

where R, $R^1$ and $R^2$ are defined hereinafter are important intermediates useful in the preparation of therapeutic 2,3,6-substituted quinazolinones which are useful as angiotensin II receptor blocking agents. The 2,3,6,7, or 8-substituted quinazolinone compounds and uses for such compounds are described in the following published European patent applications, EP-253310, EP-324377 and EP-497150.

The methods described in these prior art references for the preparation of these substituted-4(3H)-quinazolinones require high temperatures which generally give rise to appreciable quantities of undesired by-products resulting in low and variable yields of product.

As described in EP-497150, the usual method to prepare the 2,3,6,7 or 8-substituted-4(3H)-quinazolinones involves reaction of the appropriately substituted aminobenzoic acid with valeric anhydride which under high vacuum is heated to give a 3,1,4-benzoxazolinone. Upon concentration, the benzoxazolinone is then treated with ammonium hydroxide-ethyl alcohol to give the desired quinazolinone. Such methods, although useful for laboratory preparations, are less suitable for commercial scale manufacturing processes.

It has now been found that 2-alkyl-3,5,6,7 or 8-substituted-4(3H)-quinazolinone compounds may be advantageously synthesized in large scale from N-aroyl or N-acyl substituted anthranilic acids. Reaction with ethylchloroformate followed by further reaction with ammonia or a primary amine gives the desired products which are formed in higher yield and purity and with reaction workups which are less labor and time intensive than the prior art.

SUMMARY OF THE INVENTION

It is therefore an object of this invention to provide a synthetic route for the preparation of high purity 2-alkyl-3,5,6,7 or 8-substituted-4(3H)quinazolinone compounds that is well suited for both laboratory and commercial scale processes.

Extensive studies by us on the process for preparing compounds of the present invention have shown that 2-alkyl-3,5,6,7 or 8-substituted-4(3H)-quinazolinone compounds of high purity and high yield can be produced through very simple reaction procedures.

Upon further study of the specification and appended claims, further objects and advantages of this invention will become apparent to those skilled in the art.

In accordance with the present invention, 2-alkyl-3,5,6,7 or 8-substituted-4(3H)-quinazolinone compounds are prepared in a novel "one-pot" synthesis from N-aroyl or N-acyl substituted anthranilic acids as outlined in Scheme I:

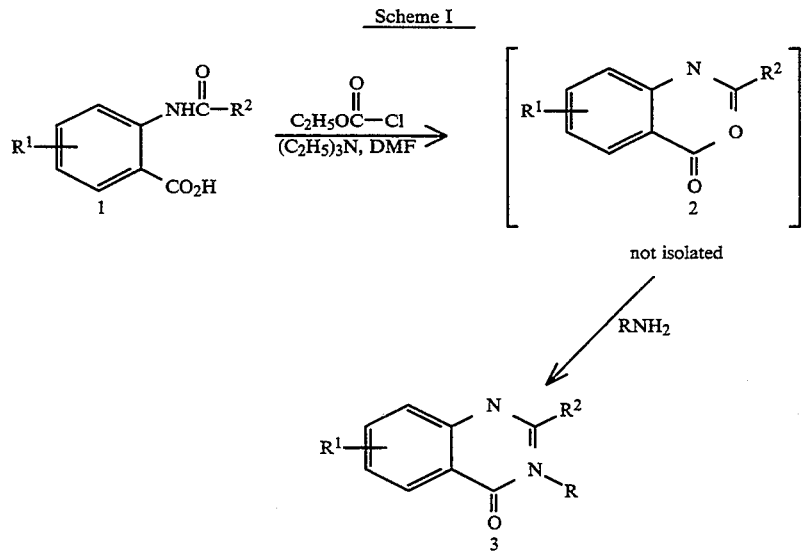

In accordance with the above reaction Scheme I, N-aroyl or N-acyl substituted anthranilic acid 1 where $R^1$ and $R^2$ are described hereinafter is reacted with ethyl chloroformate to give the substituted benzoxazolinone 2 which, without isolation, is further reacted with ammonia or a primary amine to give the desired 2-alkyl-3,5,6,7 or 8-substituted-4(3H)quinazolinone 3.

The 2-alkyl-3,5,6,7 or 8-substituted-4(3H)quinazolinone compounds which may be prepared by the present invention may be represented by the following structural formula:

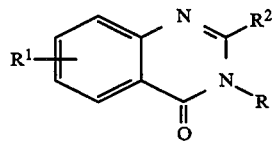

wherein:

R is selected from H, straight or branched alkyl of 1 to 9 carbon atoms, phenyl, substituted phenyl (substitution selected from mono lower alkyl of 1 to 3 carbon atoms, -CF₃, nitro, O-alkyl of 1 to 3 carbon atoms, halogen and -NH₂), benzol and substituted benzyl (substitution selected from H, halogen, phenyl and substituted phenyl (substitution selected from halogen, -CN, carboxy, carboalkoxy, tetrazole and protected tetrazole));

$R^1$ is selected from a straight or branched alkyl of 1 to 9 carbon atoms, optionally substituted with H, straight chain alkyl of 1 to 4 carbon atoms, phenyl, substituted phenyl (substitution selected from mono lower alkyl of 1 to 3 carbon atoms, -CF₃, nitro, O-alkyl of 1 to 3 carbon atoms, and NH₂), pyridine, thiophene, furan, O-straight chain alkyl of 1 to 4 carbon atoms, -OH and O-acyl with a straight chain alkyl of 1 to 4 carbon atoms and halogen;

$R^2$ is a straight chain alkyl of 1 to 6 carbon atoms. Relative to the above generic description, compounds of Formula I which are preferred are those in which: $R^1$ is selected from moieties of the formula:

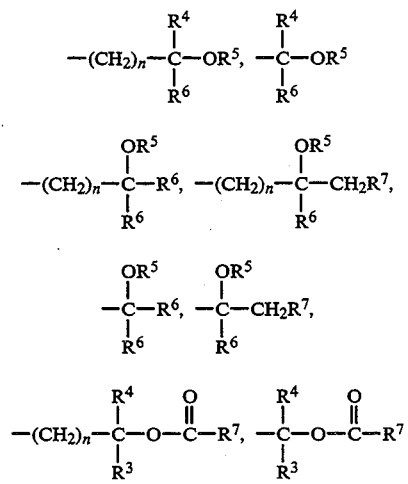

and halogen;
where $R^3$ is selected from H, straight chain lower alkyl of 1 to 4 carbon atoms, phenyl, substituted phenyl (substitution selected from mono-lower alkyl of 1 to 3 carbon atoms, -CF₃, nitro, O-alkyl of 1 to 3 carbon atoms, and NH₂), pyridine, thiophene, furan and halogen;
$R^4$ is H, straight chain lower alkyl of 1 to 4 carbon atoms, phenyl, substituted phenyl (substitution selected from mono-lower alkyl of 1 to 3 carbon atoms, -CF₃, nitro, O-alkyl of 1 to 3 carbon atoms and -NH₂), pyridine, thiophene, and furan; provided, however, that $R^3$ and $R^4$ cannot be H;
$R^5$ is selected from H, straight chain or branched lower alkyl of 1 to 4 carbon atoms;
$R^6$ is selected from straight chain lower alkyl of 1 to 4 carbon atoms, phenyl, substituted phenyl (substitution selected from mono-lower alkyl of 1 to 3 carbon atoms, -CF₃, nitro, O-alkyl of 1 to 3 carbon atoms, and -NH₂), pyridine, thiophene, and furan;

$R^7$ is selected from straight or branched lower alkyl of 1 to 4 carbon atoms; n is an integer from 1 to 3.

Furthermore, most preferred compounds of Formula I according to the present invention are those of Formula I in which:

R is selected from H, straight or branched alkyl of 1 to 9 carbon atoms, phenyl, substituted phenyl (substitution selected from mono lower alkyl of 1 to 3 carbon atoms, -CF₃, nitro, O-alkyl of 1 to 3 carbon atoms, halogen and -NH₂), benzyl, substituted benzyl (substitution selected from H, halogen, phenyl and substituted phenyl (substitution selected from halogen, -CN, carboxy, carboalkoxy, tetrazole and protected tetrazole));

$R^1$ is selected from moieties of the formula:

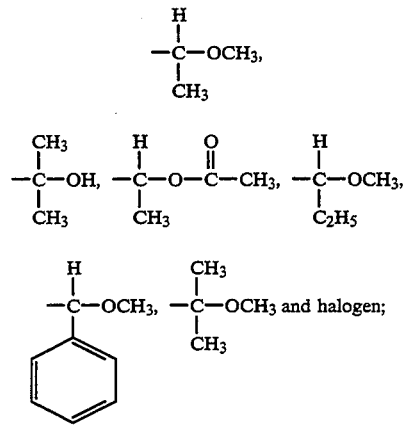

$R^2$ is a straight chain alkyl of 3 or 4 carbon atoms. Compounds of the Formula I which are most particularly preferred are those in which:

R is selected from H, straight or branched alkyl of 1 to 9 carbon atoms, phenyl, substituted phenyl (substitution selected from mono lower alkyl of 1 to 3 carbon atoms, -CF₃, nitro, O-alkyl of 1 to 3 carbon atoms, halogen or -NH₂), benzyl, substituted benzyl (substitution selected from H, halogen, phenyl and substituted phenyl (substitution selected from halogen, -CN, carboxy, carboalkoxy, tetrazole and protected tetrazole));

$R^1$ is selected from moieties of the formula:

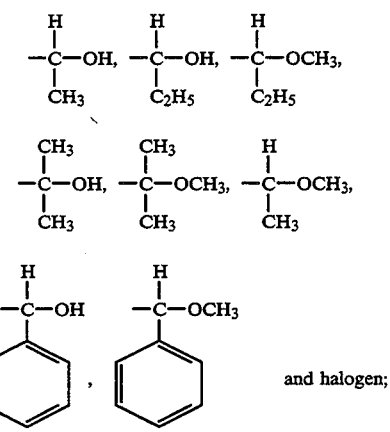

and halogen;

$R^2$ is a straight chain alkyl of 3 or 4 carbon atoms.

DESCRIPTION OF THE PREFERRED EMBODIMENTS

The process and compounds of the present invention are described in reaction Scheme I.

The improved process comprises reacting a N-aroyl or N-acyl substituted anthranilic acid having the formula:

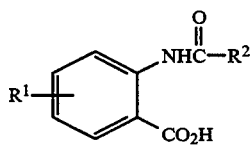

wherein $R^1$ and $R^2$ are hereinbefore defined with ethyl chloroformate in the presence of triethylamine to give the substituted benzoxazoline which is not isolated but further reacted with ammonia or a primary amine and recovering the 2-alkyl-3,5,6,7 or 8-substituted-4(3H)quinazolinone.

The reaction may be carried out in any suitable polar aprotic miscible solvent. Polar aprotic water miscible solvents suitable for use in the present invention include but are not limited to dimethyl sulfoxide(DMSO), N,N-dimethylformamide (DMF), dimethylacetamide, tetrahydrofuran, hexamethylphosphoramide (HMPA), sulfolane and dimethyl sulfone.

The preferred solvent for formation of the substituted benzoxazolinone is N,N-dimethylformamide at a preferred temperature of 0° C. to about 60° C. Further reaction with ammonium hydroxide is preferred at a temperature range of 10° C. to about 70° C.

In accordance with the preferred embodiment and with reference to reaction Scheme I, N-aroyl or N-acyl substituted anthranilic acid 1 where $R^1$ and $R^2$ are described above is dissolved in N,N-dimethylformamide containing triethylamine at 0°–46° C. followed by adding ethyl chloroformate at 35° to 60° C. Heating at 35° to 60° C. gives the substituted benzoxazolinone 2. Without isolation, ammonium hydroxide is added at 10°–15° C. followed by heating at 70° C. for 14 hours or the reaction mixture is added to preheated concentrated ammonium hydroxide at 30° to 36° C. followed by heating at 60° to 70° C. for 14 to 17 h. The reaction mixture is diluted with water, the resulting solid collected, washed with 1:1 N,N-dimethylformamide:water, water and then dried to give the desired 2-alkyl-5,6,7 or 8-substituted-4(3H)-quinazolinone 3.

It is preferred to use concentrated aqueous ammonia in excess.

The above process is an improvement over previously described literature methods. The distinct advantage being that the product is often easily isolated, not requiring high temperature and vacuum to be formed and is of higher purity and yield than previously described.

The following specific examples are provided to further illustrate this invention and the manner in which it may be carried out.

It will be understood, however, that the specific details given in the examples have been chosen for purposes of illustration and are not to be construed as a limitation of the invention.

EXAMPLE 1

2-Butyl-6-iodo-4-(3H)-quinazolinone

To a mixture of 1500 g of N-valeryl-5-iodoanthranilic acid in 14.5 L of N,N-dimethylformamide is added under nitrogen, 660 mL of triethylamine. The resulting solution is cooled to 0° to 5° C. and 432 mL of ethyl chloroformate added over 10 minutes at a rate to maintain the temperature below 10° C. The reaction mixture is heated to 35° to 50° C. for 2 hours until the evolution of carbon dioxide ceases. Analysis of a small aliquot of the reaction mixture by GC/MS indicates 93.7% (area %) conversion. The reaction mixture is cooled to 10°–15° C. and 5.0 L of concentrated ammonium hydroxide added over 10 minutes. The resulting slurry is then heated at 60°–70° C. for 14 hours. To the reaction mixture is added 10 L of water and the resulting slurry cooled to ambient temperature and filtered. The recovered solid is washed with 3 L of a 1:1 water-N,N-dimethylformamide solution followed by two 3 L water washes. The solid is dried at 50° C. to give 803 g (56.7%) of the desired product. The purity is 100% as analyzed by GC/MS.

EXAMPLE 2

2-Butyl-6-iodo-4-(3H)-quinazolinone

To 542 kg of N,N-dimethylformamide, 59.5 kg of N-valeryl-5-iodoanthranilic acid (purity of 90% by GC/MS) and 20 kg of triethylamine, while heating at 46° C. is added 17.7 kg of ethyl chloroformate with stirring over 34 minutes at 46° to 48° C. Vigorous evolution of carbon dioxide results upon the addition of the ethyl chloroformate. The resulting mixture is heated for 2.5 h at 55° to 60° C. during which time the carbon dioxide evolution ceases. The reaction mixture is then added over 45 minutes to 320 kg of concentrated ammonium hydroxide which is preheated to 36° C. The reaction mixture is then heated at 63°–64° C. for 16.5 h with stirring followed by the addition of 294 kg of water. The resulting slurry is cooled to 25° C. and filtered. The solid on the filter is washed with 112 kg of 1:1 N,N-dimethylformamide:water and twice with 115 kg of water. The white crystalline solid is dried to constant weight in a vacuum drier at 50° C. to give 47.7 kg (84.9% or 94.3% corrected for the purity of the starting material), MP 257°–258° C. Analysis by GC/MS indicates the purity of the product to exceed 99% and confirms the identity of the product: NMR 0.86 (t,3H), 1.31 (m,2H), 1.65 (q,2H), 2.54 (t,2H), 7.34 (d,1H), 8.01 (d,1H), 8.19 (s,1H), 12.28 (s,1H).

EXAMPLE 3

Preparation of 2-butyl-6-iodo-4(3H)-quinazolinone

A solution of 10.0 g of N-valeryl-5-iodoanthranilic acid and 4.60 mL of triethylamine in 100 mL of dimethylformamide is heated at 45°–50° C. and 3.03 mL of ethyl chloroformate is added dropwise with stirring over 3–5 min. Vigorous evolution of carbon dioxide followed immediately upon addition of the chloroformate. The resulting mixture is heated for 30 min. at 60° C. and then added to 60 mL (0.90 mol) of concentrated ammonium hydroxide which is pre-heated to 37° C. The reaction mixture is then heated at 60°–65° C. for 15 hr with mechanical stirring. Water (40 mL) is added and the mixture cooled to 25° C. and filtered. The solid on the filter is washed once with 20 mL of 1:1 dimethylformamide:water and twice with 20 mL of water. The white crystalline solid is then dried to constant weight in a forced air oven at 50° C. The yield of 2-butyl-6-iodo-4(3H)-quinazolinone is 7.14 g (75.6%), m.p. 257°-258° C. Analysis by GC/MS indicates purity of 100.0% (GC. area %) and confirms the identity of the product.

We claim:

1. A process for producing substituted quinazolinone compounds of Formula I:

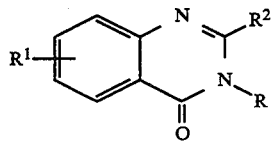

wherein

R is selected from H, straight or branched alkyl of 1 to 9 carbon atoms, phenyl, substituted phenyl (substitution selected from mono lower alkyl of 1 to 3 carbon atoms, -CF$_3$, nitro, O-alkyl of 1 to 3 carbon atoms, halogen and -NH$_2$), benzyl and substituted benzyl (substitution selected from H, halogen, phenyl and substituted phenyl (substitution selected from halogen, -CN, carboxy, carboalkoxy, tetrazole and protected tetrazole));

R$^1$ is a straight or branched alkyl of 1 to 9 carbon atoms, optionally substituted with a substituent selected from H, straight chain alkyl of 1 to 4 carbon atoms, phenyl, substituted phenyl (substitution selected from mono lower alkyl of 1 to 3 carbon atoms, -CF$_3$, nitro, O-alkyl of 1 to 3 carbon atoms, and NH$_2$), pyridine, thiophene, furan, O-straight chain alkyl of 1 to 4 carbon atoms, -OH and O-acyl with a straight chain alkyl of 1 to 4 carbon atoms and halogen;

R$^2$ is a straight chain alkyl of 1 to 6 carbon atoms which comprises:

a. reacting an N-aroyl or N-acyl substituted anthranilic acid of the formula:

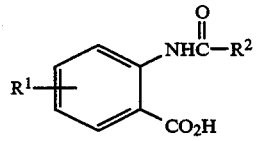

with ethyl chloroformate to produce an intermediate of the formula:

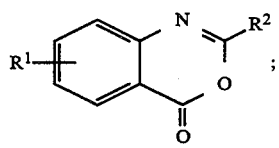

b. which is further reacted, without isolation, with aqueous ammonia or a primary amine, and c. recovering the substituted quinazolinone compound of Formula I so produced.

2. The process according to claim 1 wherein R is selected from H, straight or branched alkyl of 1 to 9 carbon atoms, phenyl, substituted phenyl (substitution selected from mono lower alkyl of 1 to 3 carbon atoms, -CF$_3$, nitro, O-alkyl of 1 to 3 carbon atoms, halogen and -NH$_2$), benzyl and substituted benzyl (substitution selected from H, halogen, phenyl and substituted phenyl (substitution selected from halogen, -CN, carboxy, carboalkoxy, tetrazole and protected tetrazole));

R$^1$ is selected from moieties of the formula:

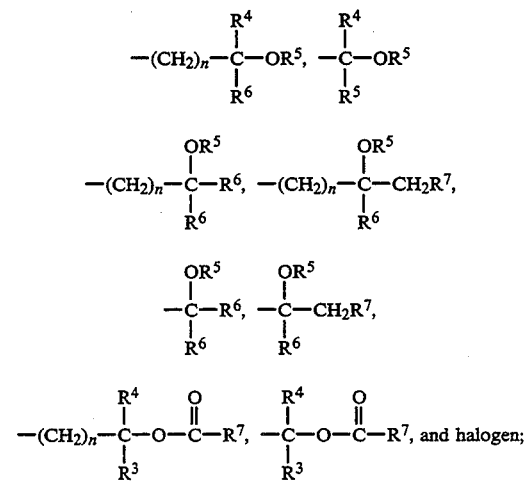

R$^2$ is a straight chain alkyl of 1 to 6 carbon atoms;

where R$^3$ is selected from H, straight chain lower alkyl of 1 to 4 carbon atoms, phenyl, substituted phenyl (substitution selected from mono-lower alkyl of 1 to 3 carbon atoms, -CF$_3$, nitro, O-alkyl of 1 to 3 carbon atoms, or NH$_2$), pyridine, thiophene, furan and halogens R$^4$ is H, straight chain lower alkyl of 1 to 4 carbon atoms, phenyl, substituted phenyl (substitution selected from mono-lower alkyl of 1 to 3 carbon atoms, -CF$_3$, nitro, O-alkyl of 1 to 3 carbon atoms and -NH$_2$), pyridine, thiophene, and furan; provided, however, that R$^3$ and R$^4$ cannot be H;

R$^5$ is selected from H, straight chain or branched lower alkyl of i to 4 carbon atoms;

R$^6$ is selected from straight chain lower alkyl of 1 to 4 carbon atoms, phenyl, substituted phenol (substitution selected from mono-lower alkyl of 1 to 3 carbon atoms, -CF$_3$, nitro, O-alkyl of 1 to 3 carbon atoms, and -NH$_2$), pyridine, thiophene, and furan;

R$^7$ is selected from straight or branched lower alkyl of 1 to 4 carbon atoms;

n is an integer from 1 to 3.

3. The process according to claim 1 wherein R is selected from H, straight or branched alkyl of 1 to 9 carbon atoms, phenyl, substituted phenyl (substitution selected from mono lower alkyl of 1 to 3 carbon atoms, -CF$_3$, nitro, O-alkyl of 1 to 3 carbon atoms, halogen and -NH$_2$), benzyl, substituted benzol (substitution selected from H, halogen, phenyl and substituted phenyl (substitution selected from halogen, -CN, carboxy, carboalkoxy, tetrazole and protected tetrazole));

R$^1$ is selected from moieties of the formula:

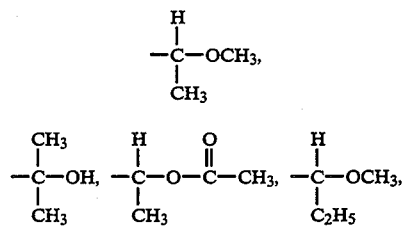

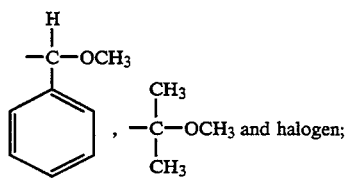

R² is a straight chain alkyl of 3 or 4 carbon atoms.

4. The process according to claim 1 wherein R is selected from H, straight or branched alkyl of 1 to 9 carbon atoms, phenyl, substituted phenyl (substitution selected from mono lower alkyl of 1 to 3 carbon atoms, -CF₃, nitro, 0-alkyl of 1 to 3 carbon atoms, halogen or -NH₂), benzyl, substituted benzyl (substitution selected from H, halogen, phenyl and substituted phenyl (substitution selected from halogen, -CN, carboxy, carboalkoxy, tetrazole and protected tetrazole));

R¹ is selected from moieties of the formula:

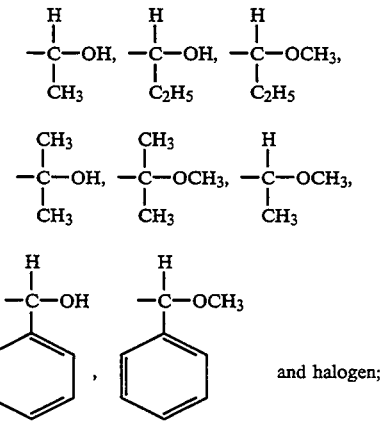

and halogen;

R² is a straight chain alkyl of 3 or 4 carbon atoms.

5. The process according to claim 1 wherein the reaction of step (a) is carried out in an aprotic, water miscible solvent in the presence of triethylamine.

6. The process of claim 4 wherein the water miscible solvent is dimethylformamide.

* * * * *